US012602774B2

(12) United States Patent
Hoffman et al.

(10) Patent No.: US 12,602,774 B2
(45) Date of Patent: Apr. 14, 2026

(54) REGIONAL PULMONARY V/Q VIA IMAGE REGISTRATION AND MULTI-ENERGY CT

(71) Applicant: University of Iowa Research Foundation, Iowa City, IA (US)

(72) Inventors: Eric Alfred Hoffman, Iowa City, IA (US); Seyed Mohammad Amin Motahari Bidgoli, Lynnwood, WA (US); Changhyun Lee, Iowa City, IA (US); Joseph Marion Reinhardt, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 897 days.

(21) Appl. No.: 17/608,433

(22) PCT Filed: May 11, 2020

(86) PCT No.: PCT/US2020/032311
§ 371 (c)(1),
(2) Date: Nov. 2, 2021

(87) PCT Pub. No.: WO2020/231904
PCT Pub. Date: Nov. 19, 2020

(65) Prior Publication Data
US 2022/0254016 A1      Aug. 11, 2022

Related U.S. Application Data

(60) Provisional application No. 62/846,394, filed on May 10, 2019.

(51) Int. Cl.
*G06K 9/00*        (2022.01)
*A61B 6/00*        (2006.01)
(Continued)

(52) U.S. Cl.
CPC ............ *G06T 7/0012* (2013.01); *A61B 6/032* (2013.01); *A61B 6/5217* (2013.01); *G06T 7/30* (2017.01);
(Continued)

(58) Field of Classification Search
CPC . G06T 2207/30061; G06T 2207/10081; G06T 7/0012; A61B 6/507; A61B 6/032; A61B 6/5217; G16H 50/30
See application file for complete search history.

(56) References Cited

U.S. PATENT DOCUMENTS 6,254,546 B1       7/2001   Vierto-Oja
2002/0198449 A1   12/2002   Baumgardner et al.
(Continued)

OTHER PUBLICATIONS

Aoki K, Izumi Y, Watanabe W, Shimizu Y, Osada H, Honda N, Itoh T, Nakayama M. Generation of ventilation/perfusion ratio map in surgical patients by dual-energy CT after xenon inhalation and intravenous contrast media. J Cardiothorac Surg. May 18, 2018;13(1):43. doi: 10.1186/s13019-018-0737-2. (Year: 2018).*
(Continued)

*Primary Examiner* — Molly Wilburn
*Assistant Examiner* — Aidan Keup
(74) *Attorney, Agent, or Firm* — Goodhue, Coleman & Owens, P.C.

(57) ABSTRACT

A method for imaging a lung of a patient is provided. The method includes acquiring a full inspiration computed tomography (CT) scan of the lung to provide a total lung capacity (TLC) image and acquiring a functional residual capacity contrast enhanced multi-energy CT scan of the lung. The method further includes processing the functional residual capacity contrast enhanced multi-energy CT scan of the lung to generate a perfused blood volume (PBV) image and a virtual non-contrast (VNC) image. The method further includes registering the TLC image to at least one of the
(Continued)

Transverse Slice          Coronal Slice

Normal

Clinical Patient

PBV and VNC images so as to provide a map of regional ventilation and to co-register local ventilation with blood perfusion, generating a lung performance metric using the co-registered images, and outputting the lung performance metric at a user interface of a computing device.

16 Claims, 8 Drawing Sheets

(51) Int. Cl.
  *A61B 6/03*        (2006.01)
  *G06T 7/00*        (2017.01)
  *G06T 7/30*        (2017.01)
(52) U.S. Cl.
  CPC .............. *G06T 2207/10081* (2013.01); *G06T 2207/30061* (2013.01)

(56)                References Cited

U.S. PATENT DOCUMENTS

| | | | |
|---|---|---|---|
| 2005/0016530 A1 | 1/2005 | McCutcheon et al. | |
| 2005/0018808 A1* | 1/2005 | Piacsek ................. | A61B 6/482 378/5 |
| 2010/0063410 A1 | 3/2010 | Avila | |
| 2015/0351714 A1 | 12/2015 | Backer | |
| 2019/0013103 A1* | 1/2019 | Henne .................... | G16H 50/30 |
| 2021/0068706 A1* | 3/2021 | De Backer ........... | A61B 5/1128 |
| 2021/0150781 A1* | 5/2021 | Shin ....................... | A61B 6/481 |

OTHER PUBLICATIONS

Hackx, M., Francotte, D., Garcia, T. S., Van Muylem, A., Walsdorff, M., & Gevenois, P. A. (2017). Effect of total lung capacity, gender and height on CT airway measurements. The British Journal of Radiology, 90(1076), 20160898. (Year: 2017).*
Computed Tomography (CT) Scan of the Chest [online]. Johns Hopkins Medicine, 2019 [retrieved on Jun. 21, 2024]. Retrieved from the internet: <URL: https://web.archive.org/web/20190420220600/https://www.hopkinsmedicine.org/health/treatment-tests-and-therapies/ct-scan-of-the-chest>. (Year: 2019) (Year: 2019).*
Andreucci, M., Solomon, R., & Tasanarong, A. (2014). Side effects of radiographic contrast media: pathogenesis, risk factors, and prevention. BioMed research international, 2014(1), 741018. (Year: 2014).*
Alford SK, van Beek EJ, McLennan G, Hoffman EA. Heterogeneity of pulmonary perfusion as a mechanistic image-based phenotype in emphysema susceptible smokers. Proc Natl Acad Sci U S A. Apr. 20, 2010;107(16):7485-90. PMCID: PMC2867701.
Chon D, Simon BA, Beck KC, Shikata H, Saba OI, Won C, Hoffman EA. Differences in regional wash-in and wash-out time constants for xenon-CT ventilation studies. Respir Physiol Neurobiol. Aug. 25, 2005;148(1-2):65-83. PubMed PMID: 16061426.
Fuld MK, Easley RB, Saba OI, Chon D, Reinhardt JM, Hoffman EA, Simon BA. CT-measured regional specific volume change reflects regional ventilation in supine sheep. J Appl Physiol (1985). Apr. 2008;104(4):1177-84. PMID: 18258804.
Fuld MK, Halaweish AF, Haynes SE, Divekar AA, Guo J, Hoffman EA. Pulmonary perfused blood volume with dual-energy CT as surrogate for pulmonary perfusion assessed with dynamic multidetector CT. Radiology. Jun. 2013;267(3):747-56. PMCID: PMC3662901.
Fuld MK, Halaweish AF, Newell JD Jr, Krauss B, Hoffman EA. Optimization of dual-energy xenon-computed tomography for quantitative assessment of regional pulmonary ventilation. Invest Radiol. Sep. 2013;48(9):629-37. PMCID: PMC3873149.
Hachulla AL, Pontana F, Wemeau-Stervinou L, Khung S, Faivre JB, Wallaert B, Cazaubon JF, Duhamel A, Perez T, Devos P, Remy J, Remy-Jardin M. Krypton ventilation imaging using dual-energy CT in chronic obstructive pulmonary disease patients: initial experience. Radiology. Apr. 2012;263(1):253-9. PMID: 22332068.

Hoffman EA, Chon D. Computed tomography studies of lung ventilation and perfusion. Proc Am Thorac Soc. 2005;2(6):492-8, 506. Review. PMCID: PMC2713338.
Hoffman EA, Lynch DA, Barr RG, van Beek EJ, Parraga G; IWPFI Investigators. Pulmonary CT and MRI phenotypes that help explain chronic pulmonary obstruction disease pathophysiology and outcomes. J Magn Reson Imaging. Mar. 2016;43(3):544-57. PMCID: PMC5207206.
Hoffman et al., "A Structural and Functional Assessment of the Lung via Multidetector-Row Computed Tomography", Proceedings of the American Thoracic Society vol. 3. pp. 519-534, 2006.
Hueper K, Vogel-Claussen J, Parikh MA, Austin JH, Bluemke DA, Carr J, Choi J, Goldstein TA, Gomes AS, Hoffman EA, Kawut SM, Lima J, Michos ED, Post WS, Po MJ, Prince MR, Liu K, Rabinowitz D, Skrok J, Smith BM, Watson K, Yin Y, Zambeli-Ljepovic AM, Barr RG. Pulmonary Microvascular Blood Flow in Mild Chronic Obstructive Pulmonary Disease and Emphysema. The MESA COPD Study. Am J Respir Crit Care Med. Sep. 1, 2015;192(5):570-80. PMCID: PMC4595687.
Hughes, JM, Glazier, JB, Maloney, JE, West, JB. Effect of lung volume on the distribution of pulmonary blood flow in man. Respir. Physiol. 1968; 4: 58-72.
International Search Report & Written Opinion, PCT/US2020/032311, Aug. 12, 2020, 15 pages.
Ishii Y, Itoh H, Suzuki T, Yonekura Y, Mukai T, Torizuka K. Quantitative assessment of ventilation-perfusion mismatch by radioxenon imaging of the lung. J Nucl Med. Jun. 1978;19(6):607-14. PubMed PMID: 660273.
Kruger SJ, Nagle SK, Couch MJ, Ohno Y, Albert M, Fain SB. Functional imaging of the lungs with gas agents. J Magn Reson Imaging. Feb. 2016;43(2):295-315. PMCID: PMC4733870.
Lee SW, Lee SM, Shin SY, Park TS, Oh SY, Kim N, Hong Y, Lee JS, Oh YM, Lee SD, Seo JB. Improvement in Ventilation-Perfusion Mismatch after Bronchoscopic Lung Volume Reduction: Quantitative Image Analysis. Radiology. Oct. 2017;285(1):250-260. doi: 10.1148/radiol.2017162148. Epub May 16, 2017. PubMed PMID: 28510483.
Milic-Emili J, Henderson JA, Dolovich MB, Trop D, Kaneko K. Regional distribution of inspired gas in the lung. J Appl Physiol. May 1966;21(3):749-59. PMID: 5912744.
Newell JD Jr, Fuld MK, Allmendinger T, Sieren JP, Chan KS, Guo J, Hoffman EA. Very low-dose (0.15 mGy) chest CT protocols using the COPDGene 2 test object and a third-generation dual-source CT scanner with corresponding third-generation iterative reconstruction software. Invest Radiol. Jan. 2015;50(1):40-5. PMCID: PMC4294320.
Ohno Y, Fujisawa Y, Takenaka D, Kaminaga S, Seki S, Sugihara N, Yoshikawa T. Comparison of Xenon-Enhanced Area-Detector CT and Krypton Ventilation SPECT/CT for Assessment of Pulmonary Functional Loss and Disease Severity in Smokers. AJR Am J Roentgenol. Feb. 2018;210(2): W45-W53. PMID: 29220212.
Pelgrim GJ, van Hamersvelt RW, Willemink MJ, Schmidt BT, Flohr T, Schilham A, Milles J, Oudkerk M, Leiner T, Vliegenthart R. Accuracy of iodine quantification using dual energy CT in latest generation dual source and dual layer CT. Eur Radiol. Sep. 2017;27(9):3904-3912. PMCID: PMC5544802.
Remy-Jardin M, Pistolesi M, Goodman LR, Gefter WB, Gottschalk A, Mayo JR, Sostman HD. Management of suspected acute pulmonary embolism in the era of CT angiography: a statement from the Fleischner Society. Radiology. Nov. 2007;245(2):315-29. Epub Sep. 11, 2007. Review. PMID: 17848685.
Sá RC, Henderson AC, Simonson T, Arai TJ, Wagner H, Theilmann RJ, Wagner PD, Prisk GK, Hopkins SR. Measurement of the distribution of ventilation-perfusion ratios in the human lung with proton MRI: comparison with the multiple inert-gas elimination technique. J Appl Physiol (1985). Jul. 1, 2017;123(1):136-146. PMCID: PMC5538816.
Vidal Melo MF, Layfield D, Harris RS, O'Neill K, Musch G, Richter T, Winkler T, Fischman AJ, Venegas JG. Quantification of regional ventilation-perfusion ratios with PET. J Nucl Med. Dec. 2003;44(12):1982-91. PubMed PMID: 14660725.
West, JB, Dollery, CT, Naimark, A. Distribution of blood flow in isolated lung; relation to vascular and alveolar pressures. J. Appl. Physiol. 1964; 19: 713-724. PMID: 14195584.

(56)  References Cited

OTHER PUBLICATIONS

Anthonisen NR, Milic-Emili J. Distribution of pulmonary perfusion in erect man. J Appl Physiol. May 1966;21(3):760-766. PMID: 5912745.

Faby S, Kuchenbecker S, Sawall S, Simons D, Schlemmer HP, Lell M, Kachelrieß M. Performance of today's dual energy CT and future multi energy CT in virtual non-contrast imaging and in iodine quantification: A simulation study. Med Phys. Jul. 2015;42(7):4349-66. PMID: 26133632.

Hoffman EA, Tajik JK, Kugelmass SD. Matching pulmonary structure and perfusion via combined dynamic multislice CT and thin-slice high-resolution CT. Comput Med Imaging Graph. Jan.-Feb. 1995;19(1):101-12. PubMed PMID: 7736410.

Holley HS, Dawson A, Bryan AC, Milic-Emili J, Bates DV. Effect of oxygen on the regional distribution of ventilation and perfusion in the lung. Can J Physiol Pharmacol. Jan. 1966;44(1):89-93. PMID: 5938995.

International Preliminary Report on Patentability, PCT/US2020/032311, Nov. 25, 2021, 10 pages.

Kaneko K, Milic-Emili J, Dolovich MB, Dawson A, Bates DV. Regional distribution of ventilation and perfusion as a function of body position. J Appl Physiol. May 1966;21(3):767-77. PMID: 5912746.

Thomas KS, Mann A, Williams J. Pulmonary (V/Q) Imaging. J Nucl Med Technol. Jun. 2018;46(2):87-88. PMID: 29871994.

* cited by examiner

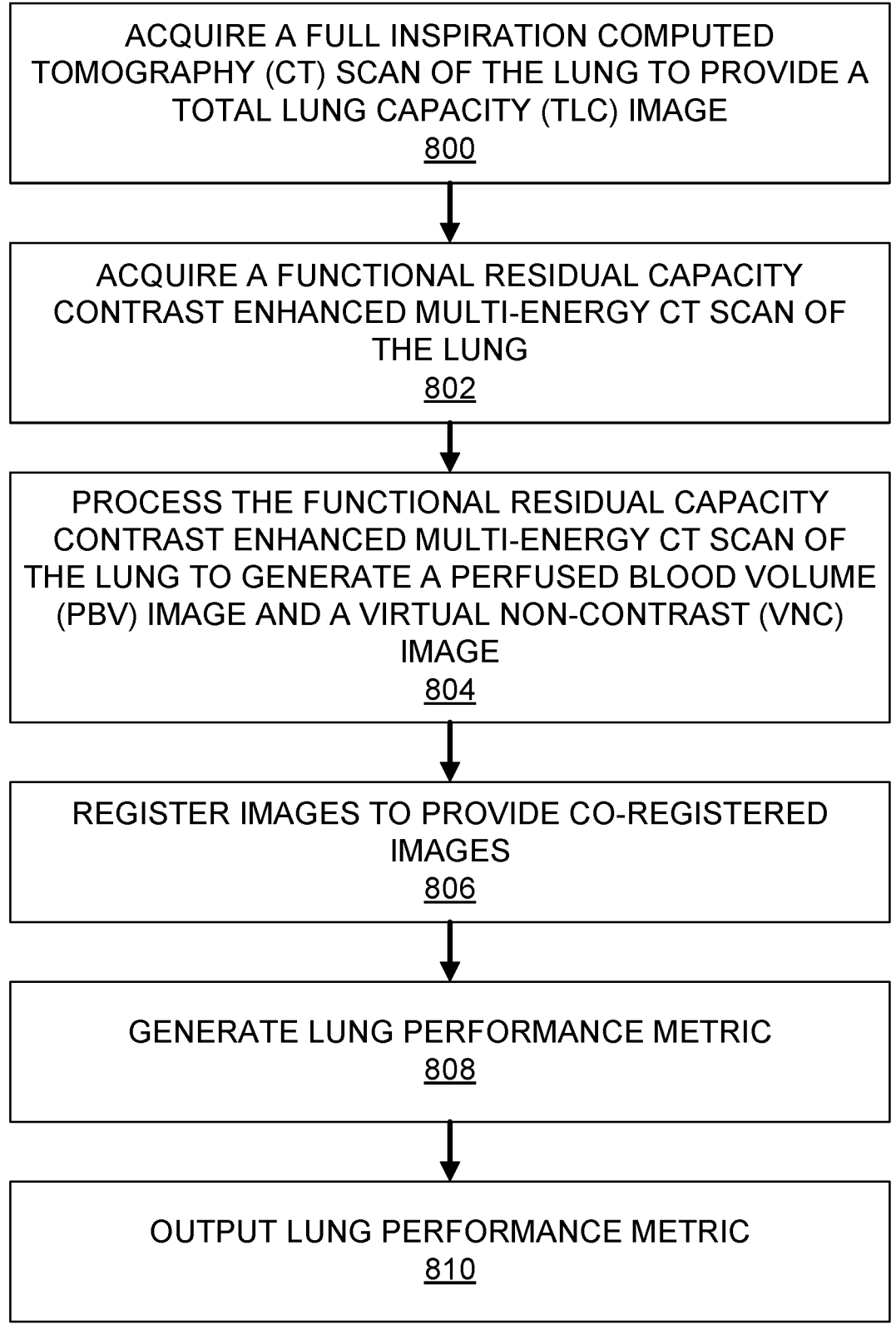

ACQUIRE A FULL INSPIRATION COMPUTED TOMOGRAPHY (CT) SCAN OF THE LUNG TO PROVIDE A TOTAL LUNG CAPACITY (TLC) IMAGE
800

ACQUIRE A FUNCTIONAL RESIDUAL CAPACITY CONTRAST ENHANCED MULTI-ENERGY CT SCAN OF THE LUNG
802

PROCESS THE FUNCTIONAL RESIDUAL CAPACITY CONTRAST ENHANCED MULTI-ENERGY CT SCAN OF THE LUNG TO GENERATE A PERFUSED BLOOD VOLUME (PBV) IMAGE AND A VIRTUAL NON-CONTRAST (VNC) IMAGE
804

REGISTER IMAGES TO PROVIDE CO-REGISTERED IMAGES
806

GENERATE LUNG PERFORMANCE METRIC
808

OUTPUT LUNG PERFORMANCE METRIC
810

FIG. 8

REGIONAL PULMONARY V/Q VIA IMAGE REGISTRATION AND MULTI-ENERGY CT

RELATED APPLICATIONS

This application claims priority to U.S. Provisional Patent Application No. 62/846,394, filed May 10, 2019, hereby incorporated by reference in its entirety.

GRANT REFERENCE

This invention was made with government support under R01 HL130883 and R01 HL112986 awarded by the National Institutes of Health. The government has certain rights in the invention.

FIELD OF THE INVENTION

The present invention relates to medical imaging. More particularly, but not exclusively, the present invention relates to regional pulmonary ventilation/perfusion (V/Q) via image registration and multi-energy computed tomography (CT).

BACKGROUND

The primary function of the lung is to match the inflow of fresh gas with the delivery of venous blood to allow for the exchange of oxygen and carbon dioxide. The basis for functional impairment associated with the majority of lung diseases comes from the mismatch between pulmonary ventilation (V) and perfusion (Q). Early research into the determinants of V and Q within the lung came from the works of John West (14, 26) and others (2, 12, 16, 19) who used radio-nuclear imaging to demonstrate the gravitational dependence of perfusion distribution within the lung (16, 19).

Clinically, ventilation has been assessed via the use of radioactive xenon gas and various radio nuclear tags of perfusion including technetium labeled macroaggregated albumin (9, 24). Dynamic CT imaging has been used to assess regional perfusion (1, 6, 9, 10) using iodinated contrast medium and regional ventilation has been assessed by dynamic and single breath CT methods using stable xenon and krypton gas (7, 8, 21). Magnetic resonance imaging (MRI) has been used to assess regional ventilation using hyperpolarized xenon and hyperpolarized helium gas as well as fluorinated gases and high concentration oxygen (11, 17) and perfusion MRI (13, 24) has utilized gadolinium contrast agents and more conventional arterial spin labeling. Positron emission tomography (PET) has been used to assess regional matching of pulmonary ventilation and perfusion, V/Q, utilizing 13NN injections and using arrival and subsequent clearance (26).

With the emergence of multidetector-row computed tomography (MDCT) and MDCT-dual energy computed tomography (DECT) assessment of regional pulmonary perfused blood volume via use of an iodinated contrast agent has been shown to provide an index of regional perfusion (6), and non-contrast imaging at multiple lung inflation steps has been shown to yield a warping function which serves as an index of regional ventilation (5). Most image matching methodology use a paradigm whereby regional organ mass is preserved when the image is warped. Additionally, perfused blood volume is best assessed with the lungs held at functional residual capacity (FRC) since at higher lung volumes, capillary beds are compressed, and regional blood volume is distorted. Lung structure is best assessed at full inflation or total lung capacity (TLC) without the use of contrast agents. When perfused blood volume is imaged via use of an iodine contrast media and DECT a material decomposition method is used to quantify regional iodine (6, 7, 22), and to generate a virtual non-contrast image (4) of the lung at FRC.

Using image registration methods, the TLC lung image is warped to the FRC virtual non-contrast image, generating an image of ventilation (regional Jacobians) which is precisely mapped to the perfused blood volume image. If both regional ventilation and regional perfusion are expressed as percent of whole lung perfused blood volume or whole lung ventilation respectively, both ventilation and perfusion are in the same units and an image of pulmonary V/Q is derived. The borders of the lung and lung lobes can be identified by use of previously described lung segmentation algorithms (11).

Thus, distributions of ventilation, perfusion and V/Q can be quantitated for lobes, right and left lung or for the whole lung. By defining normal V/Q as lung regions with a value between, for instance, 0.8 and 1.2, high V/Q (ventilated but under perfused) as regions, for instance above 1.2, and low V/Q (poorly ventilated but perfused) as regions, for instance, below 0.8. the percentage of high, normal and low V/Q regions can be expressed for the whole lung or whatever lung subdivision is of interest. With these regional assessments of lung function, in conjunction with the anatomic resolution of computed tomography, we provide a simple to perform, low radiation dose, relatively inexpensive methodological breakthrough in the clinical characterization of pulmonary pathophysiology.

While dual energy CT has been demonstrated to be the most reliable tool for the assessment of pulmonary emboli (23) nuclear medicine derived V/Q scans (25) have remained a means of assessing the physiologic impact of a perfusion deficit. While there are various imaging modalities to acquire quantitative assessments of ventilation or perfusion deficits, none of these imaging modalities, other than the traditional nuclear medicine V/Q scan, have proven a practical, reliable means of providing quantitative assessments of pulmonary functional deficits along with a detailed assessment of lung structure.

Nuclear medicine V/Q scans are often deemed non-diagnostic because of the poor resolution of the methodology. With the introduction of $3^{rd}$ generation (Siemens SOMATOM Force along with other manufacturer's following this lead) dual energy CT with double the spatial resolution, higher contrast resolution and imaging at up to 10 times lower radiation doses (20) it is now possible to acquire a lung perfusion scan with half the conventional iodine concentration at very low radiation doses (1-2 mSv or less) in a breath hold of just 2-3 seconds or less. While dual energy CT also offers the possibility of imaging regional ventilation with the use of stable xenon gas and some have reportedly derived V/Q scans from separate DECT imaging of xenon and iodine delivery protocols (18), xenon gas is expensive, it has unwanted anesthetic effects such as elimination of the drive to breath or anesthesia. Additionally, results from the ventilation maneuver is highly dependent upon the ventilatory depth and rate and thus is much more difficult to control in a clinical setting. This method is unlikely to be adopted widely.

Therefore, improved methods, systems, and devices for V/Q scans are needed, especially to provide for generating lung performance maps and metrics which may be used to among other things, make pre/post-surgery evaluation of patients in lieu of nuclear medicine methods of V/Q evaluation.

SUMMARY

By imaging at TLC without contrast agents, images provide anatomic details related to lung status and image warping of the TLC lung to the FRC virtual non-contrast lung image provides a measure of ventilation as well as other metrics related to lung mechanics such as a measure of isotropic vs anisotropic expansion. According to one aspect, the present invention provides a protocol for the implementation of a coached non-contrast breath hold scan at TLC and a DECT PBV scan at FRC which provides for the quantitation of regional ventilation, perfusion and V/Q reported for the whole lung or any lung subdivision of interest.

Therefore, it is a primary object, feature, or advantage of the present invention to improve over the state-of-the-art.

It is a further object, feature, or advantage of the present invention to provide a method for evaluating lung function.

A still further object, feature, or advantage of the present invention is to provide for generating lung performance maps and metrics which may be used to make pre/post-surgery evaluation of patients without using nuclear medicine methods of V/Q evaluation.

Another object, feature, or advantage is to provide images of lungs which have improved resolution and contrast.

Yet another object, feature, or advantage is to provide images of lungs in a manner which is faster, less expensive, and provides better functional and anatomical information for lung lobar analysis than prior art approaches.

A further object, feature, or advantage is to provide for combining two lung CT images, one taken at full inspiration and another at relaxed expiration using a contrast agent (e.g. iodine) to generate a ventilation/perfusion (V/Q) map showing basic physiological structures of the lung.

A still further object, feature, or advantage is to generate detailed V/Q maps to provide physicians with better physiological and anatomical information for disease diagnosis/assessment and surgical intervention and planning.

Another object, feature, or advantage is to provide for imaging suitable in the presence of key clinical indications such as, but not limited to:

Identification and quantification of the functional effect of chronic or acute pulmonary embolism Quantification of lobar function prior to pulmonary surgery (wedge resections or lobectomy associated with lung cancer)

Assessment of early lung transplant rejection

Evaluation of the functional deficits associated with inflammatory lung diseases such as chronic obstructive pulmonary disease (COPD), pulmonary fibrosis, acute respiratory distress syndrome, etc.

Characterization of primary and secondary pulmonary hypertension

Identification of the basis for acute exacerbations associated with chronic obstructive pulmonary disease Assessment of pulmonary perfusion or V/Q status associated with cardiac or valvular dysfunction One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a method for imaging a lung of a patient includes acquiring a full inspiration computed tomography (CT) scan of the lung, acquiring a functional residual capacity contrast enhanced multi-energy CT scan of the lung, processing the full inspiration CT scan of the lung and the functional residual capacity contrast enhanced multi-energy CT scan of the lung to co-register local ventilation with blood perfusion in the lung, generating at least one lung performance metric by processing the scans, and outputting the lung performance metric at a user interface of a computing device.

According to another aspect, a system for assessing and displaying lung function of a lung of a patient includes a display, a processor, and software executable by the processor stored on a non-transitory computer readable medium. The software is configured to process a full inspiration computed tomography (CT) scan of the lung and a functional residual capacity contrast enhanced multi-energy CT scan of the lung. The software is further configured to process the full inspiration CT scan of the lung and the functional residual capacity contrast enhanced multi-energy CT scan of the lung to co-register local ventilation with blood perfusion in the lung. The software is further configured to generate at least one lung performance metric and present the at least one lung performance metric at a user interface of a computing device.

According to another aspect, a method for imaging a lung of a patient is provided. The method includes acquiring a full inspiration computed tomography (CT) scan of the lung to provide a total lung capacity (TLC) image and acquiring a functional residual capacity contrast enhanced multi-energy CT scan of the lung. The method further includes processing the functional residual capacity contrast enhanced multi-energy CT scan of the lung to generate a perfused blood volume (PBV) image and a virtual non-contrast (VNC) image. The method further includes registering the TLC image to at least one of the PBV image and the VNC image so as to co-register local ventilation with blood perfusion in the lung and provide co-registered images, generating a lung performance metric using the co-registered images, and outputting the lung performance metric at a user interface of a computing device. The image processing of the TLC, non-contrast enhanced, scan can include identification of, for instance, the lung lobes as well as sub-lobar segments such that when registered to the FRC lung image one can evaluate V, Q and V/Q based upon individual anatomic components of the lung.

According to yet another aspect, a system for assessing and displaying lung function of a lung of a patient is provided. The system includes a display, a processor, software executable by the processor stored on a non-transitory computer readable medium. The software is configured to process a functional residual capacity contrast enhanced multi-energy CT scan of the lung to generate a perfused blood volume (PBV) image and a virtual non-contrast (VNC) image, register a total lung capacity (TLC) image acquired from a full inspiration computed tomography (CT) scan of the lung to at least one of the PBV image and the VNC image so as to co-register local ventilation with blood perfusion in the lung and provide co-registered images, generate at least one lung performance metric by processing the co-registered images, and output the at least one lung performance metric at a user interface of a computing device.

BRIEF DESCRIPTION OF THE DRAWINGS

Illustrated embodiments of the disclosure are described in detail below with reference to the attached drawing figures, which are incorporated by reference herein.

FIG. 8 illustrates an example of a method

DETAILED DESCRIPTION

Figure 1:
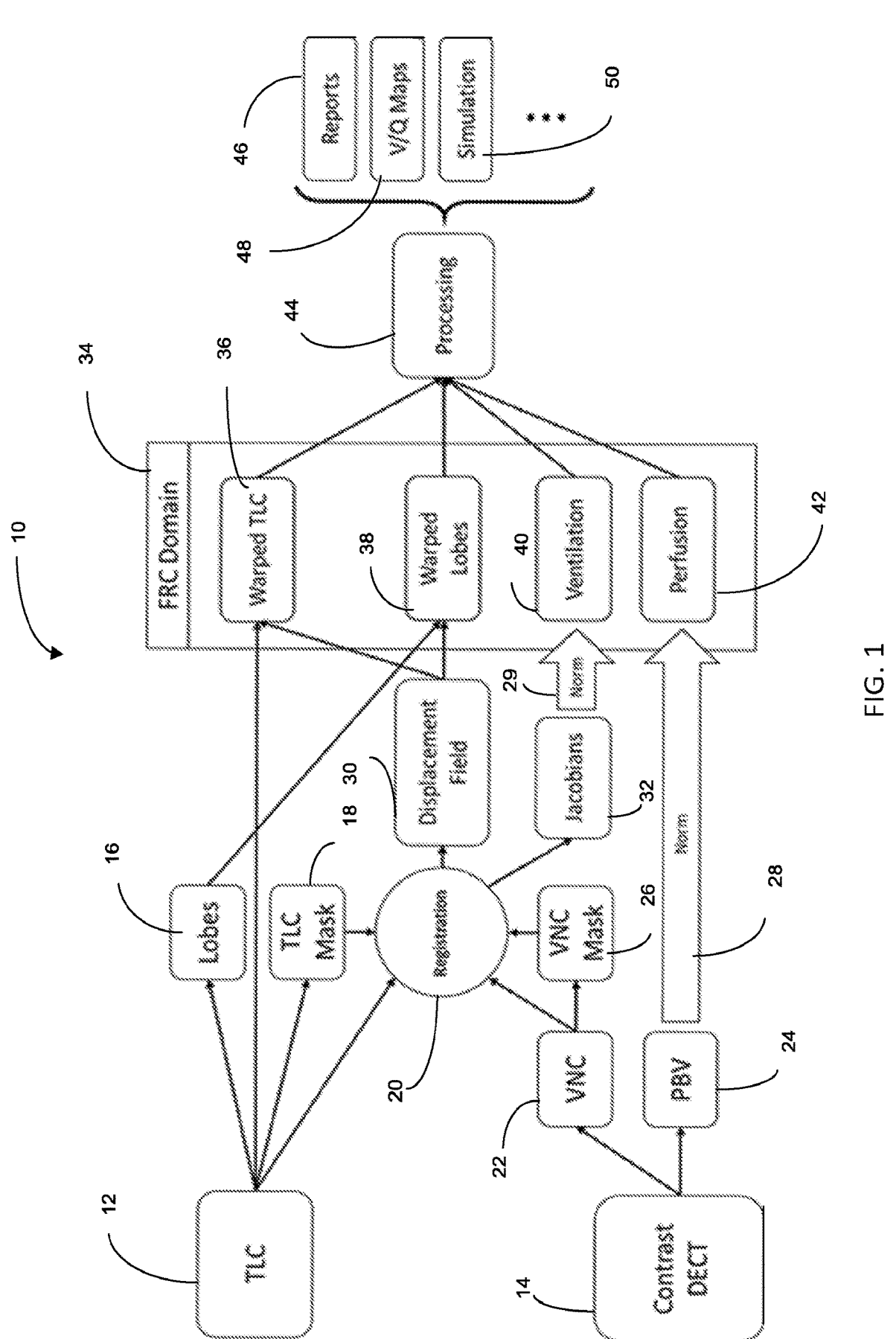
FIG. 1 is block diagram of one example.

According to one aspect, the present invention involves applying image registration to an inspiration scan (such as a full inspiration CT) and an expiratory scan (such as a functional residual capacity) contrast enhanced multi-Energy CT in order to 25 generate local ventilation maps which are co-registered with blood perfusion in the lung. The co-registered images can be used to derive a lung performance metric such as pulmonary Ventilation/Perfusion maps. According to another aspect, the present invention provides for using the lung performance maps and metrics generated to make pre/post-surgery evaluation of the patients in lieu of nuclear medicine methods of V/Q evaluation. The block diagram of a sample system 10 is depicted in FIG. 1. Two CT images of the patient acquired in a single session are used. Although the term "image" is used, it is to be understood that an "image" may be a set of volumetric images. The goal is to take two images at different lung volumes to assess regional ventilation. For instance, the first image 12 may be acquired at full inspiration or Total Lung Capacity (TLC) (3-5 seconds with current technology).

The second CT image 14 may be used to assess the perfused blood volume (surrogate for perfusion) in the lung and as such it is generally acquired at Functional Residual Capacity of the lung. Blood volume in the lung can be evaluated using image processing algorithms. However, to evaluate the perfusion accurately an enhancement contrast agent like iodine may be injected to the patient. In this case the contrast injection can follow a predefined protocol to make sure it is homogenously distributed in the lung before the CT image is taken. When using contrast enhancement, the second image 14 can be taken in multi spectrum mode to allow material decomposition. Using standard three material decomposing algorithms separating Air-water and iodine two separate images 22, 24 are generated. The first image 24 is an iodine map that is called a Perfused Blood Volume (PBV) image 24. The second image is a virtual non-contrast image 22 that shows X-ray attenuation levels as if there was no contrast injected. It is called a Virtual Non-Contrast (VNC) image 22 as shown in FIG. 1. Thus, the functional residual capacity contrast enhanced multi-energy CT scan of the lung may be processed to generate a perfused blood volume (PBV) image and a virtual non-contrast (VNC) image.

In the next step the TLC image 12 is passed to segmentation algorithms to generate Lung and lobes masks. VNC image 22 is also segmented to generate the FRC level lung mask. 3D CT images (TLC 12, PBV 24 (FRC), VNC 22 (FRC) are passed to the processing software 44 after registration. The software 44 may apply any number of steps to generate a report 46 and a lung performance map.

Segmentation

By segmenting the inspiratory (ideally TLC) image 12 into the right and left lung, lobes and sub-lobar segments (lobes 16) and using the displacement field 30 generated by the registration step 20 to warp it (warped lobes 38) on the PBV image reports summarizing the functional status of individual lung anatomy can be generated. Any number of different image processing methods may be used to provide the segmentation such as various types of thresholding algorithms, classification methods, clustering methods, and hybrid methods.

Registration

Lung segmentation is applied to TLC 12 and VNC images 22 to generate lung masks (18, 26). This is an optional step to improve the performance of the registration algorithm by masking out the areas that do not need to be registered (outside lung). For registering TLC 12 and VNC images 22, either of them can be selected as the fixed image. However, if TLC 12 is selected as the fixed image then the PBV should also be moved into TLC domain using the displacement field of the registration from VNC-FRC image so that all the images end up being registered to TLC. This registration 20 can be performed using any appropriate image registration method and one may assume registration to VNC here. The output of the registration 20 is the warped image 36 along with the displacement field 30 and the Jacobians 32.

Thus, the TLC image may be registered to at least one of the PBV image and the VNC image so as to co-register local ventilation with blood perfusion in the lung and provide co-registered images.

Calculating Regional Ventilation

Regional Ventilation (REV) may be calculated using Jacobian determinants from the registration step. However, any method that uses regional volume changes between two images may be used here. This results in another 3D map that is registered to the selected fixed image.

Normalization

Absolute REV or PBV values depend on the volumes at which the scans are performed. Similarly, the absolute values in the PBV image depend on iodine concentration in the blood, cardiac output among other parameters. To minimize dependence on such parameters one may normalize 28, 29 these two maps by total lung volume change and total PBV so that each region on these maps shows the portion of ventilation 40 or perfusion 42 of the whole lung that is present in that region respectively.

Calculate Performance Maps

Figure 2:
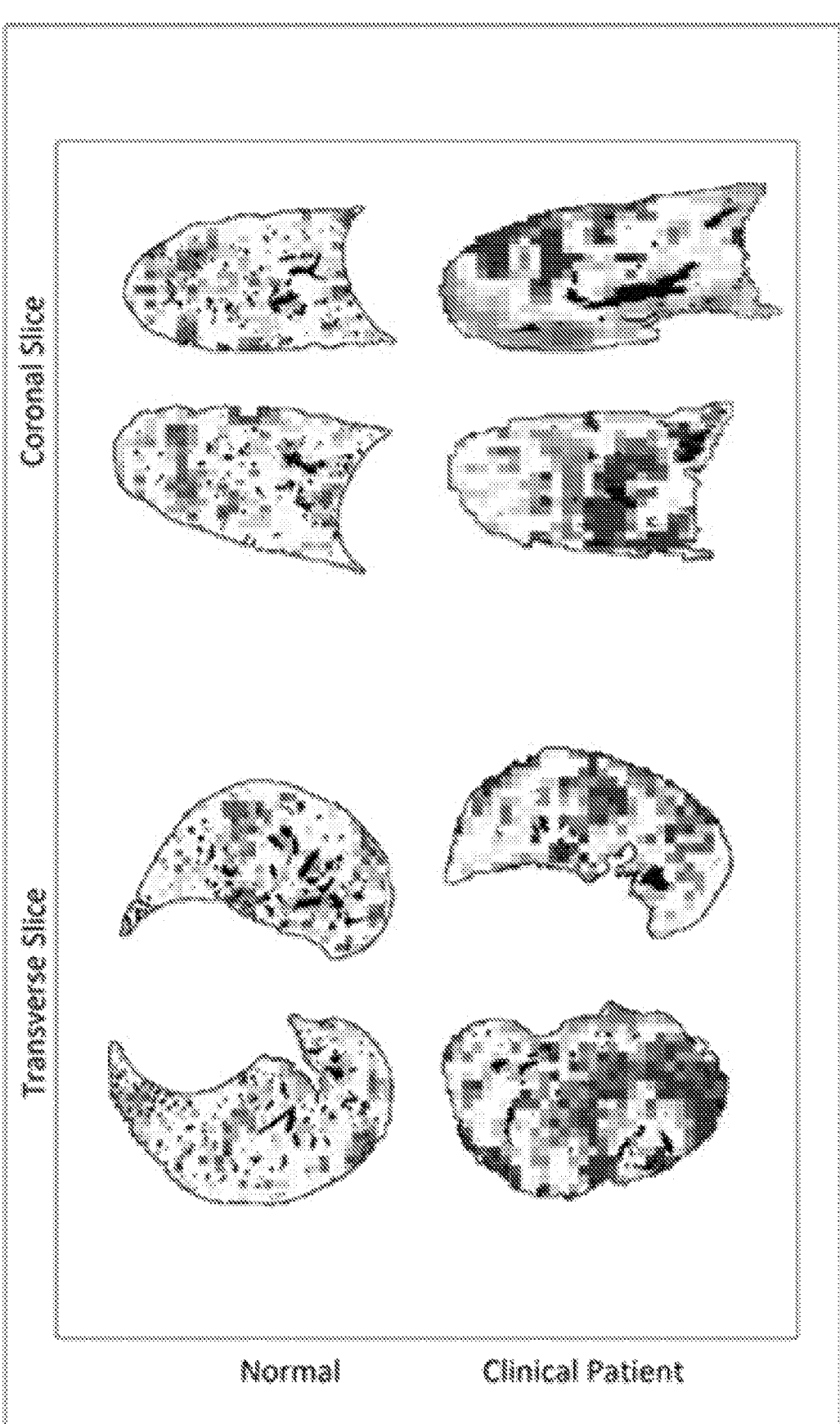
FIG. 2 is an example of a performance map. Normal V/Q is in white and gray levels show deviations from normal V/Q, either high or low. Color coding of this scale provides more easily recognizable differences.
Figure 3:
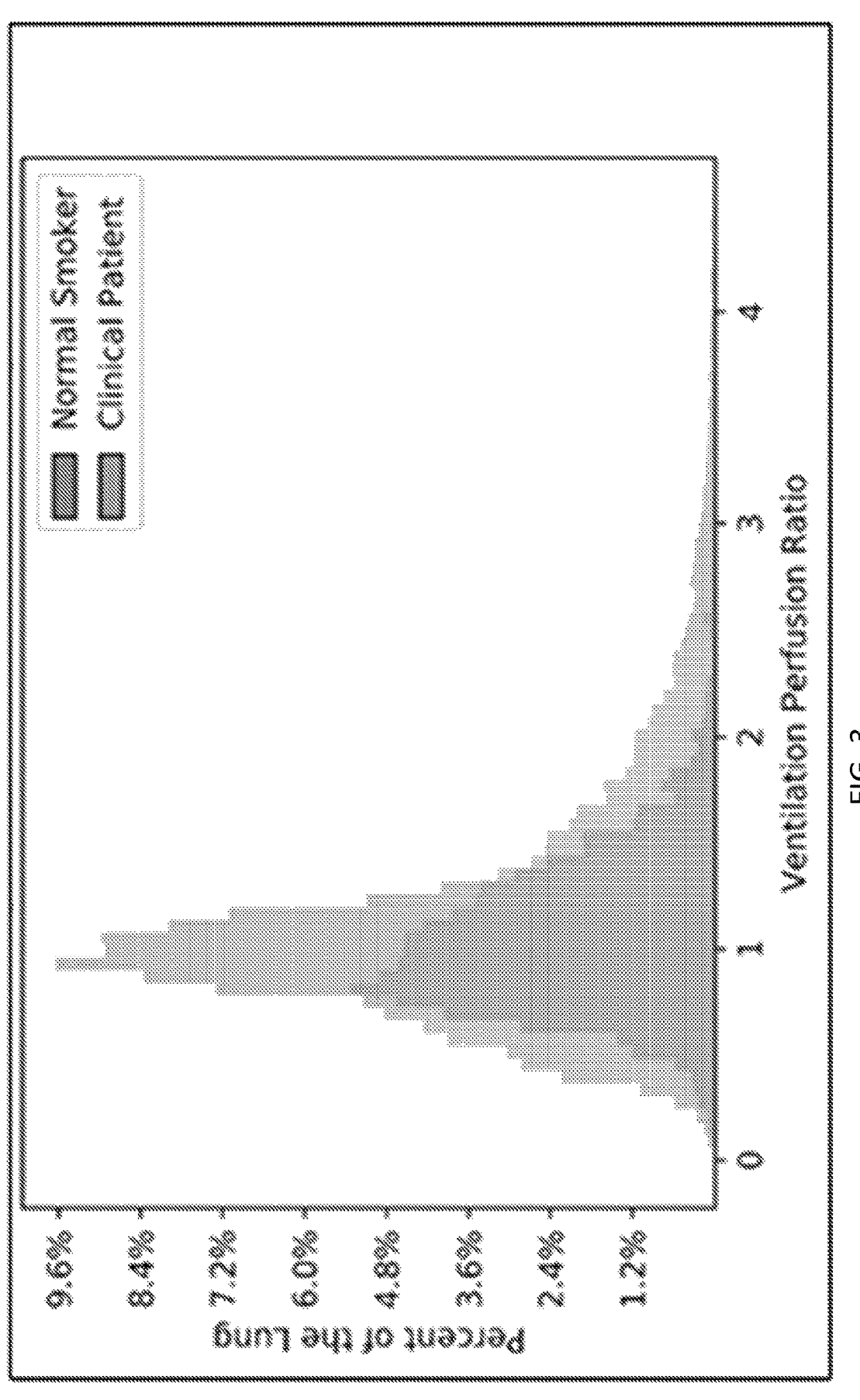
FIG. 3 illustrates histograms corresponding to FIG. 2. Plotted are the percent of lung regions with a particular V/Q ratio. The Normal subject has a narrow histogram centered around 1 while the patient has a wider histogram with a greater number of regions in the higher range, indicating regions of ventilation with poor perfusion, This sort of plot is commonly produced in color better differentiation of histograms.

Now that all 4 images/maps are in the same volume level (expiration (FRC) Domain box 34) a performance map can be defined for the lung. To avoid extreme values due to noise the performance can be calculated on blocks of voxels such as cubical regions of fixed size. Performance in each cubical region may be defined using the values from any combination of the 4 maps in that region. As an example, it may be defined as average REV divided by average PBV when all the non-perfused areas are removed from the performance map. Such images are shown in FIG. 2. Corresponding histograms are shown in FIG. 3.

Generate Regional Report

Using the performance map and all the registered images reports 46 may be compiled for different lobes/regions of the lung. The software may also provide a simulation 50 which simulates removing a region of interest from the lung and calculating the performance for the remaining areas of the lung to ensure the patient can sustain the removal of the selected areas by surgery.

Sample Results

Figure 4:
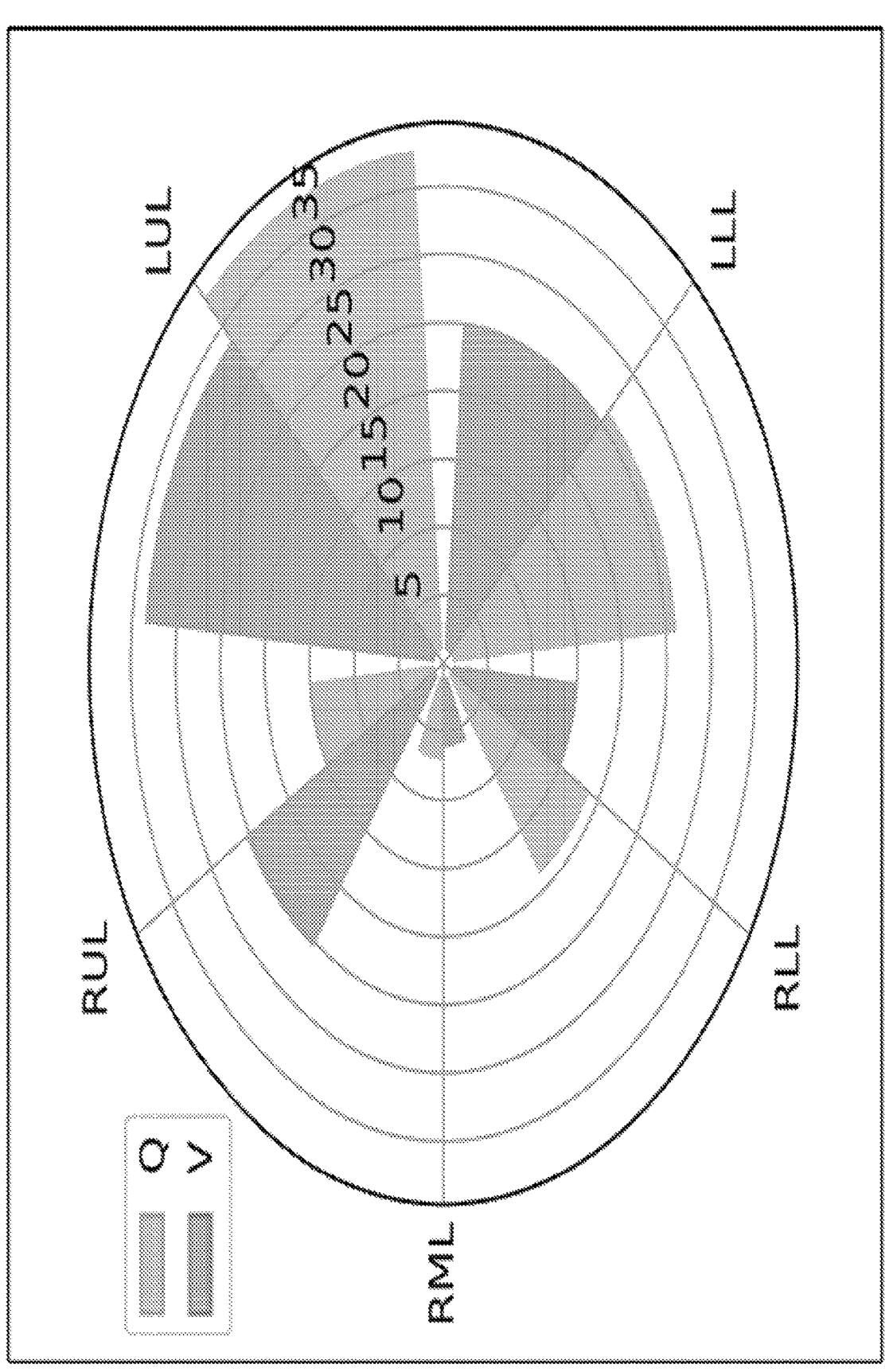
FIG. 4 illustrates Lobar distribution of ventilation (V) and Perfusion (Q). LLL: left lower lobe; LUL: left upper lobe; RUL: right upper lobe; RML: right middle lobe; RLL: right lower lobe. Percent of the total ventilation or perfusion to the whole lung is represented by the distance to which each wedge reaches relative to the rings.

An example of possible results using the lobar masks is shown in FIG. 4 for a subject diagnosed with Pulmonary Embolism (PE) in Right Upper Lobe (RUL). Regional ventilation and perfusion are integrated in each lobe and quantify how much of the whole ventilation and perfusion is assigned to each lobe respectively. While these plots don't show the VQ mismatch that is not consistent within a lobe they are very informative in lung surgery preplanning which requires knowledge on how ventilation and perfusion are distributed between lobes. These results give a general idea of how much performance will be lost if a lobe is to be removed.

Figure 5:
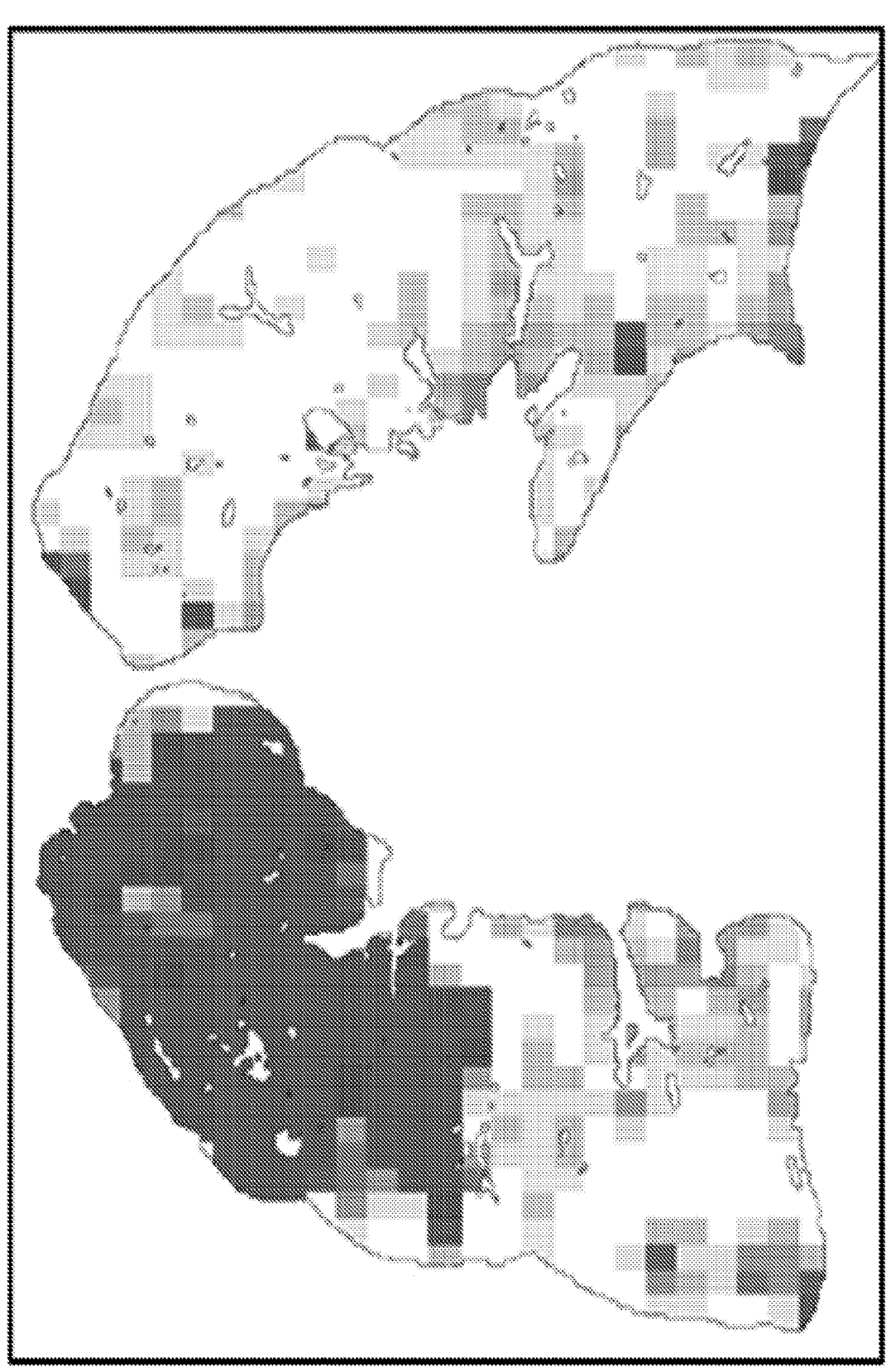
FIG. 5 is a V/Q map of the patient with a pulmonary emboli in right upper lobe. Different colors may be used represent V/Q. For example, shades of blue may be used to represent higher than normal V/Q (i.e. low Q and/or high V) and shades of red may be used to represent lower than normal V/Q (i.e. low ventilation and/or high Q). Blue regions may be used represent areas of the lung where pulmonary emboli were restricting blood flow.
Figure 6:
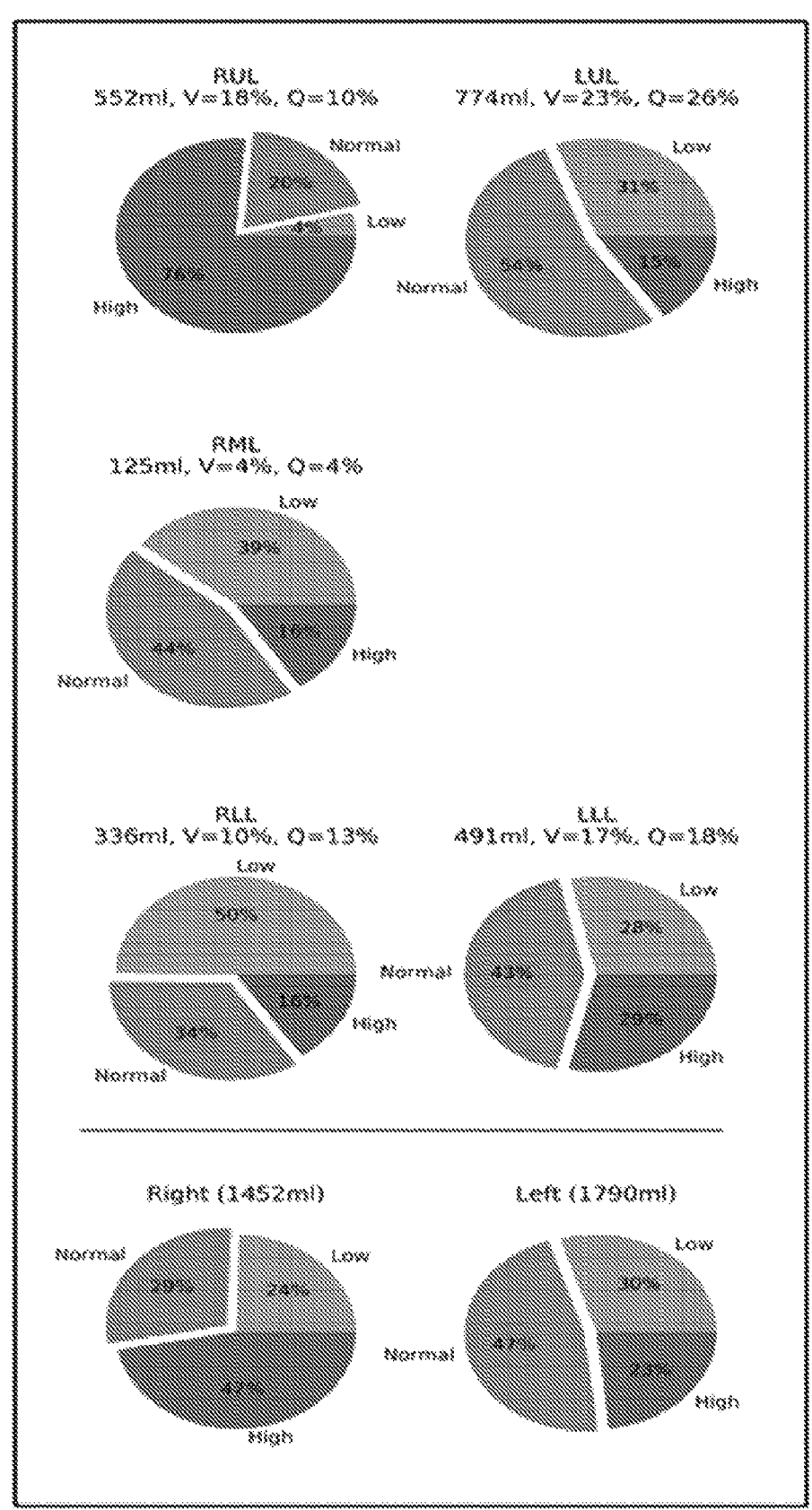
FIG. 6 provides pie charts demonstrating the relative percentages of normal, low and high V/Q per lobes and right/Left lung. Such charts can be displayed for any sub-anatomic regions of the lung, and high, normal and low ranges can be adjusted based on population data. A surgeon, for example, could use the plots to determine the contribution of a given lung lobe to the over-all ventilation and perfusion. If the contribution is too high relative to other lobes, an alternative treatment may be necessary rather than to remove that lob as an intervention for lung cancer.

Using the lobar masks along with the V/Q maps of the lung we can determine the distribution of low, normal and high V/Q regions in each lobe. Such plots for the sample PE subject are shown in FIG. 6. It is clearly seen that 76% of RUL has high V/Q which means the perfusion is less than the corresponding ventilation. The 3D map of the V/Q 5 can be used directly by the radiologist to localize regions of VQ mismatch within the lung as shown in FIG. 5.

Computing Machine Architecture

Figure 7:
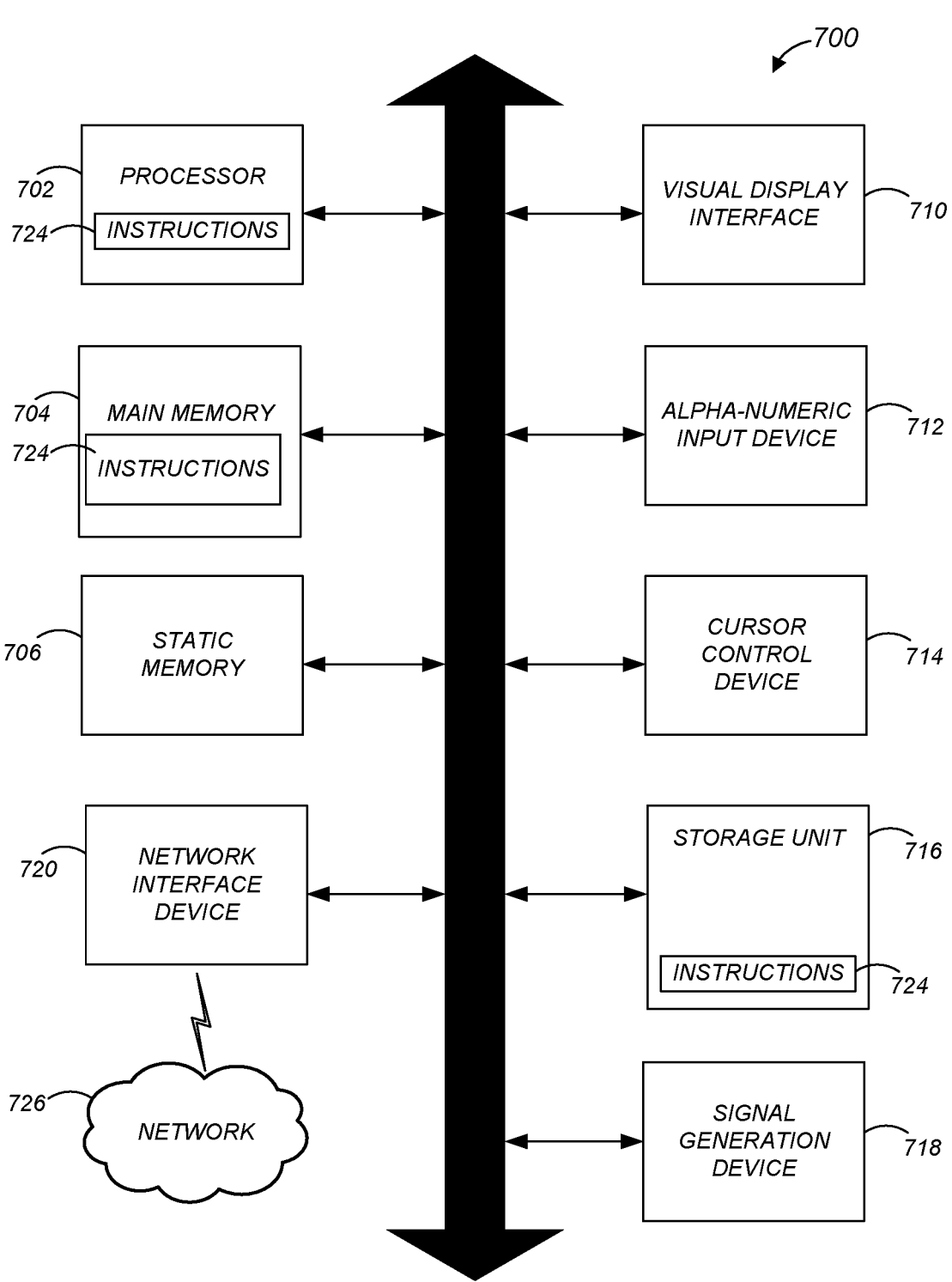
FIG. 7 illustrates one example of a computing system.

FIG. 7 is a block diagram illustrating components of an example machine able to read instructions from a machine-readable medium and execute them in a processor (or controller). Specifically, FIG. 7 shows a diagrammatic representation of a machine in the example form of a computer system 700 within which program code (e.g., software) for causing the machine to perform any one or more of the methodologies discussed herein may be executed. The program code may be comprised of instructions 724 executable by one or more processors 702. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment. It is contemplated that the machine may be in operative communication with medical imaging devices or integrated into the medical imaging devices.

The machine may be a server computer, a client computer, a personal computer (PC), a tablet PC, or any machine capable of executing instructions 724 (sequential or otherwise) that specify actions to be taken by that machine. Further, while only a single machine is illustrated, the term "machine" shall also be taken to include any collection of machines that individually or jointly execute instructions 724 to perform any one or more of the methodologies discussed herein.

The example computer system 700 includes a processor 702 (e.g., a central processing unit (CPU), a graphics processing unit (GPU), a digital signal processor (DSP), one or more application specific integrated circuits (ASICs), a main memory 704, and a static memory 706, which are configured to communicate with each other via a bus 708. The computer system 700 may further include visual display interface 710 such as may be used for displaying output in the form previously expressed, including that shown in the figures. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 710 may include or may interface with a touch enabled screen. The computer system 700 may also include alphanumeric input device 712 (e.g., a keyboard or touch screen keyboard), a cursor control device 714 (e.g., a mouse, a trackball, a joystick, a motion sensor, or other pointing instrument), a storage unit 716, a signal generation device 718 (e.g., a speaker), and a network interface device 620, which also are configured to communicate via the bus 608.

The storage unit 716 includes a machine-readable medium 722 on which is stored instructions 724 (e.g., software) embodying any one or more of the methodologies or functions described herein. The instructions 724 (e.g., software) may also reside, completely or at least partially, within the main memory 704 or within the processor 702 (e.g., within a processor's cache memory) during execution thereof by the computer system 700, the main memory 704 and the processor 702 also constituting machine-readable media. The instructions 724 (e.g., software) may be transmitted or received over a network 726 via the network interface device 720.

While machine-readable medium 722 is shown in an example embodiment to be a single medium, the term "machine-readable medium" should be taken to include a single medium or multiple media (e.g., a centralized or distributed database, or associated caches and servers) able to store instructions (e.g., instructions 724). The term "machine-readable medium" shall also be taken to include any medium that is capable of storing instructions (e.g., instructions 724) for execution by the machine and that cause the machine to perform any one or more of the methodologies disclosed herein. The term "machine-readable medium" includes, but not be limited to, data repositories in the form of solid-state memories, optical media, and magnetic media.

The computer system 700 may be configured for assessing and displaying lung function of a lung of a patient. Software in the form of instructions 724 may be executable by the processor 702 and stored on a non-transitory computer readable medium such as the main memory 704. The software is configured to process a functional residual capacity contrast enhanced multi-energy CT scan of the lung to generate a perfused blood volume (PBV) image and a virtual non-contrast (VNC) image, register a total lung capacity (TLC) image acquired from a full inspiration computed tomography (CT) scan of the lung to at least one of the PBV image and the VNC image so as to co-register local ventilation with blood perfusion in the lung, generate at least one lung performance metric by processing the full inspiration CT scan of the lung and the functional residual capacity contrast enhanced multi-energy CT scan of the lung, and output the at least one lung performance metric at a user interface of a computing device. The user interface may be, for example, the visual interface 710.

FIG. 8 further illustrates an overview of a method. In step 800 a full inspiration computed tomography (CT) scan of the lung to provide a total lung capacity (TLC) image is acquired. In step 802, a functional residual capacity contrast enhanced multi-energy CT scan of the lung is acquired. These scans may be acquired in a single session. In step 804, the functional residual capacity contrast enhanced multi-energy CT scan of the lung is processed to generate a perfused blood volume (PBV) image and a virtual non-contrast (VNC) image. In step 806, the TLC image is registered to at least one of the PBV image and the VNC image as previously explained so as to co-register local ventilation with blood perfusion in the lung and provide co-registered images. In step 808, a lung performance metric is generated using the co-registered images. In step 810, the lung performance metric is output at a user interface of a computing device.

The invention is not to be limited to the particular embodiments described herein. In particular, the invention contemplates numerous variations in the specific methodologies used, the manner in which the software is implemented, the hardware used, and other variations. It is to also be understood that although various image processing methods, algorithms, and techniques are disclosed herein, the present invention contemplates that other appropriate image processing methodologies may be used including for image segmentation, image registration, and image analysis. In addition, the image acquisition protocol may be further standardized, and various algorithms described herein may be used in any number of different environments.

The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

REFERENCES

The following references cited herein are incorporated by reference in their entireties.

1. Alford S K, van Beek E J, McLennan G, Hoffman E A. Heterogeneity of pulmonary perfusion as a mechanistic image-based phenotype in emphysema susceptible smokers. Proc Natl Acad Sci USA. 2010 Apr. 20; 107(16):7485-90. PMCID: PMC2867701.

2. Anthonisen N R, Milic-Emili J. Distribution of pulmonary perfusion in erect man. J Appl Physiol. 1966 May; 21(3):760-6. PMID: 5912745.

3. Chon D, Simon B A, Beck K C, Shikata H, Saba 01, Won C, Hoffman E A. Differences in regional wash-in and wash-out time constants for xenon-CT ventilation studies. Respir Physiol Neurobiol. 2005 Aug. 25; 148 (1-2):65-83. PubMed PMID: 16061426.

4. Faby S, Kuchenbecker S, Sawall S, Simons D, Schlemmer H P, Lell M, Kachelrieß M. Performance of today's dual energy CT and future multi energy CT in virtual non-contrast imaging and in iodine quantification: A simulation study. Med Phys. 2015 July; 42(7):4349-66. PMID: 26133632.

5. Fuld M K, Easley R B, Saba O I, Chon D, Reinhardt J M, Hoffman E A, Simon B A. CT-measured regional specific volume change reflects regional ventilation in supine sheep. J Appl Physiol (1985). 2008 April; 104 (4):1177-84. PMID: 18258804.

6. Fuld M K, Halaweish A F, Haynes S E, Divekar A A, Guo J, Hoffman E A. Pulmonary perfused blood volume with dual-energy CT as surrogate for pulmonary perfusion assessed with dynamic multidetector CT. Radiology. 2013 June; 267(3):747-56. PMCID: PMC3662901.

7. Fuld M K, Halaweish A F, Newell J D Jr, Krauss B, Hoffman E A. Optimization of dual-energy xenon-computed tomography for quantitative assessment of regional pulmonary ventilation. Invest Radiol. 2013 September; 48(9):629-37. PMCID: PMC3873149.

8. Hachulla A L, Pontana F, Wemeau-Stervinou L, Khung S, Faivre J B, Wallaert B, Cazaubon J F, Duhamel A, Perez T, Devos P, Remy J, Remy-Jardin M. Krypton ventilation imaging using dual-energy CT in chronic obstructive pulmonary disease patients: initial experience. Radiology. 2012 April; 263(1):253-9. PMID: 22332068.

9. Hoffman E A, Chon D. Computed tomography studies of lung ventilation and perfusion. Proc Am Thorac Soc. 2005; 2(6):492-8, 506. Review. PMCID: PMC2713338.

10. Hoffman E A, Tajik J K, Kugelmass S D. Matching pulmonary structure and perfusion via combined dynamic multislice CT and thin-slice high-resolution CT. Comput Med Imaging Graph. 1995 January-February; 19(1):101-12. PubMed PMID: 7736410.

11. Hoffman E A, Lynch D A, Barr R G, van Beek E J, Parraga G; IWPFI Investigators. Pulmonary CT and MRI phenotypes that help explain chronic pulmonary obstruction disease pathophysiology and outcomes. J Magn Reson Imaging. 2016 March; 43(3):544-57. PMCID: PMC5207206.

12. Holley H S, Dawson A, Bryan A C, Milic-Emili J, Bates D V. Effect of oxygen on the regional distribution of ventilation and perfusion in the lung. Can J Physiol Pharmacol. 1966 January; 44(1):89-93. PMID: 5938995.

13. Hueper K, Vogel-Claussen J, Parikh M A, Austin J H, Bluemke D A, Carr J, Choi J, Goldstein T A, Gomes A S, Hoffman E A, Kawut S M, Lima J, Michos E D, Post W S, Po M J, Prince M R, Liu K, Rabinowitz D, Skrok J, Smith B M, Watson K, Yin Y, Zambeli-Ljepovic A M, Barr R G. Pulmonary Microvascular Blood Flow in Mild Chronic Obstructive Pulmonary Disease and Emphysema. The MESA COPD Study. Am J Respir Crit Care Med. 2015 Sep. 1; 192(5):570-80. PMCID: PMC4595687.

11

12

14. Hughes, J M, Glazier, J B, Maloney, J E, West, J B. Effect of lung volume on the distribution of pulmonary blood flow in man. Respir. Physiol. 1968; 4: 58-72.

15. Ishii Y, Itoh H, Suzuki T, Yonekura Y, Mukai T, Torizuka K. Quantitative assessment of ventilation-perfusion mismatch by radioxenon imaging of the lung. J Nucl Med. 1978 June; 19(6):607-14. PubMed PMID: 660273.

16. Kaneko K, Milic-Emili J, Dolovich M B, Dawson A, Bates D V. Regional distribution of ventilation and perfusion as a function of body position. J Appl Physiol. 1966 May; 21(3):767-77. PMID: 5912746.

17. Kruger S J, Nagle S K, Couch M J, Ohno Y, Albert M, Fain S B. Functional imaging of the lungs with gas agents. J Magn Reson Imaging. 2016 February; 43(2): 295-315. PMCID: PMC4733870

18. Lee S W, Lee S M, Shin S Y, Park T S, Oh S Y, Kim N, Hong Y, Lee J S, Oh Y M, Lee S D, Seo J B. Improvement in Ventilation-Perfusion Mismatch after Bronchoscopic Lung Volume Reduction: Quantitative Image Analysis. Radiology. 2017 October; 285(1):250-260. doi: 10.1148/radio1.2017162148. Epub 2017 May 16. PubMed PMID: 28510483.

19. Milic-Emili J, Henderson J A, Dolovich M B, Trop D, Kaneko K. Regional distribution of inspired gas in the lung. J Appl Physiol. 1966 May; 21(3):749-59. PMID: 5912744.

20. Newell J D Jr, Fuld M K, Allmendinger T, Sieren J P, Chan K S, Guo J, Hoffman E A. Very low-dose (0.15 mGy) chest CT protocols using the COPDGene 2 test object and a third-generation dual-source CT scanner with corresponding third-generation iterative reconstruction software. Invest Radiol. 2015 January; 50(1): 40-5. PMCID: PMC4294320.

21. Ohno Y, Fujisawa Y, Takenaka D, Kaminaga S, Seki S, Sugihara N, Yoshikawa T. Comparison of Xenon-Enhanced Area-Detector CT and Krypton Ventilation SPECT/CT for Assessment of Pulmonary Functional Loss and Disease Severity in Smokers. AJR Am J Roentgenol. 2018 February; 210(2): W45-W53. PMID: 29220212.

22. Pelgrim G J, van Hamersvelt R W, Willemink M J, Schmidt B T, Flohr T, Schilham A, Milles J, Oudkerk M, Leiner T, Vliegenthart R. Accuracy of iodine quantification using dual energy CT in latest generation dual source and dual layer CT. Eur Radiol. 2017 September; 27(9):3904-3912. PMCID: PMC5544802.

23. Remy-Jardin M, Pistolesi M, Goodman L R, Gefter W B, Gottschalk A, Mayo J R, Sostman H D. Management of suspected acute pulmonary embolism in the era of CT angiography: a statement from the Fleischner Society. Radiology. 2007 November; 245(2):315-29. Epub 2007 Sep. 11. Review. PMID: 17848685.

24. Sá R C, Henderson A C, Simonson T, Arai T J, Wagner H, Theilmann R J, Wagner P D, Prisk G K, Hopkins S R. Measurement of the distribution of ventilation-perfusion ratios in the human lung with proton MRI: comparison with the multiple inert-gas elimination technique. J Appl Physiol (1985). 2017 Jul. 1; 123(1): 136-146. PMCID: PMC5538816.

25. Thomas K S, Mann A, Williams J. Pulmonary (V/Q) Imaging. J Nucl Med Technol. 2018 June; 46(2):87-88. PMID: 29871994

26. Vidal Melo M F, Layfield D, Harris R S, O'Neill K, Musch G, Richter T, Winkler T, Fischman A J, Venegas J G. Quantification of regional ventilation-perfusion ratios with PET. J Nucl Med. 2003 December; 44(12): 1982-91. PubMed PMID: 14660725.

27. West, J B, Dollery, C T, Naimark, A. Distribution of blood flow in isolated lung; relation to vascular and alveolar pressures. J. Appl. Physiol. 1964; 19: 713-724. PMID: 14195584

What is claimed is:

1. A method for imaging a lung of a patient, the method comprising:

acquiring a full inspiration computed tomography (CT) scan of the lung to provide a total lung capacity (TLC) image without use of a contrasting agent;

acquiring a functional residual capacity contrast enhanced multi-energy CT scan of the lung;

processing the functional residual capacity contrast enhanced multi-energy CT scan of the lung to generate a perfused blood volume (PBV) image and a virtual non-contrast (VNC) image;

registering the TLC image to at least one of the PBV image and the VNC image so as to co-register local ventilation with blood perfusion in the lung and provide co-registered images;

generating a lung performance metric using the co-registered images; and outputting the lung performance metric at a user interface of a computing device.

2. The method of claim 1 wherein the at least one lung performance metric comprises a pulmonary ventilation/perfusion (V/Q) map.

3. The method of claim 1 wherein the at least one lung performance metric is represented as a histogram illustrating a ventilation perfusion ratio.

4. The method of claim 1 wherein the at least one lung performance metric is represented as a Lobar distribution of ventilation (V) and perfusion (Q).

5. The method of claim 1 wherein the at least one lung performance metric is represented as a set of pie charts demonstrating relative percentages of normal, low and high V/Q per lobes and right/Left lung.

6. The method of claim 1 further comprising using the at least one lung performance metric in making a pre-surgery evaluation or a post-surgery evaluation of the patient.

7. The method of claim 1 wherein the full inspiration computed tomography (CT) scan of the lung and the functional residual capacity contrast enhanced multi-energy CT scan of the lung are acquired in a single session.

8. The method of claim 1 wherein an enhancement contrast agent is used in acquiring the functional residual capacity contrast enhanced multi-energy CT scan of the lung.

9. The method of claim 8 wherein a multi spectrum mode is used in acquiring the functional residual capacity contrast enhanced multi-energy CT scan of the lung.

10. A system for assessing and displaying lung function of a lung of a patient, the system comprising:

a display;

a processor;

software executable by the processor stored on a non-transitory computer readable medium, the software configured to:

process a functional residual capacity contrast enhanced multi-energy CT scan of the lung to generate a perfused blood volume (PBV) image and a virtual non-contrast (VNC) image;

register a total lung capacity (TLC) image acquired from a full inspiration computed tomography (CT) scan of the lung without contrast agent to at least one of the PBV image and the VNC image so as to co-register local ventilation with blood perfusion in the lung to provide co-registered images;

generate at least one lung performance metric using the co-registered images; and output the at least one lung performance metric at a user interface of a computing device.

11. The system of claim 10 wherein the at least one lung performance metric comprises a pulmonary ventilation/perfusion (V/Q) map.

12. The system of claim 10 wherein the at least one lung performance metric is represented as a histogram illustrating a ventilation perfusion ratio.

13. The system of claim 10 wherein the at least one lung performance metric is represented as a Lobar distribution of ventilation (V) and perfusion (Q).

14. The system of claim 10 wherein the at least one lung performance metric is represented as a set of pie charts demonstrating relative percentages of normal, low and high V/Q per lobes and right/left lung.

15. The system of claim 10 wherein the at least one lung performance metric is used in making one of a pre surgery evaluation and a post surgery evaluation of the patient.

16. The system of claim 10 wherein the full inspiration computed tomography (CT) scan of the lung and the functional residual capacity contrast enhanced multi-energy CT scan of the lung are acquired in a single session.

\* \* \* \* \*